US00PP24030P3

(12) United States Plant Patent
Podaras

(10) Patent No.: US PP24,030 P3
(45) Date of Patent: Nov. 19, 2013

(54) ***BUDDLEIA* PLANT NAMED 'HINEBUD2'**

(50) Latin Name: *Buddleia*
Varietal Denomination: Hinebud2

(75) Inventor: Peter C. Podaras, Davis, CA (US)

(73) Assignee: Hines Growers, Inc., Fallbrook, CA (US)

( * ) Notice: Subject to any disclaimer, the term of this patent is extended or adjusted under 35 U.S.C. 154(b) by 90 days.

(21) Appl. No.: 13/385,241

(22) Filed: Feb. 9, 2012

(65) Prior Publication Data

US 2013/0212756 P1 Aug. 15, 2013

(51) Int. Cl.
*A01H 5/00* (2006.01)

(52) U.S. Cl.
USPC ..... Plt./242

(58) Field of Classification Search
USPC ..... Plt./242
See application file for complete search history.

*Primary Examiner* — Kent L Bell
(74) *Attorney, Agent, or Firm* — Barbara Campbell; Cochran Freung & Young LLC

(57) ABSTRACT

A *Buddleia* plant particularly distinguished by an upright and dense growth habit, large, inflorescences that are upright-curved with a rounded tip, and is a plant suitable for use in hanging baskets, containers, and beddings, is disclosed.

2 Drawing Sheets

Genus and species: *Buddleia* hybrid (complex hybrid of *Buddleia davidii*×*Buddleia alternifolia*×*Buddleia caryopterifolia*×*Buddleia lindleyana*×*Buddleia crispa*).

Variety denomination: 'Hinebud2'.

BACKGROUND OF THE NEW PLANT

The present invention comprises a new and distinct variety of *Buddleia,* botanically known as *Buddleia* hybrid, and hereinafter referred to by the variety name 'Hinebud2'. The new variety originated from a cross-pollination conducted in Winters, Calif. in July 2010 between the female *Buddleia* parent, an un-named seedling (unpatented) and the male *Buddleia* parent, (*Buddleia davidii*×*B. alternifolia*)×*B. davidii* 'Podaras #12' (U.S. Plant Pat. No. 22,098). The female parent is a complex hybrid of *Buddleia davidii*×*Buddleia alternifolia*×*Buddleia caryopterifolia*×*Buddleia lindleyana*× *Buddleia crispa.* A single plant selection was subsequently chosen for further evaluation and asexual propagation.

The new plant was first asexually propagated on Sep. 15, 2010 in Winters, Calif. and has been asexually reproduced by cuttings for three generations in Winters, Calif. The present invention has been found to retain its distinctive characteristics through successive asexual propagations by softwood cuttings.

'Hinebud2' has not been made publicly available or sold more than one year prior to the filing of this application.

SUMMARY OF THE INVENTION

The following are the most outstanding and distinguishing characteristics of the new variety when grown under normal horticultural practices in Winters, Calif.

1. An upright and dense growth habit;
2. Large, inflorescences that are upright-curved with a rounded tip; and
3. For use in hanging baskets, containers and beddings.

DESCRIPTION OF THE PHOTOGRAPHS

This new *Buddleia* plant is illustrated by the accompanying photographs which show the overall plant habit, foliage and inflorescence of the plant. The colors are as true as can be reasonably obtained by conventional photographic procedures. The photographs are of a one-year old plant grown in a greenhouse and outdoors in Winters, Calif. in August 2011.

DESCRIPTION OF THE NEW VARIETY

Figure 1:
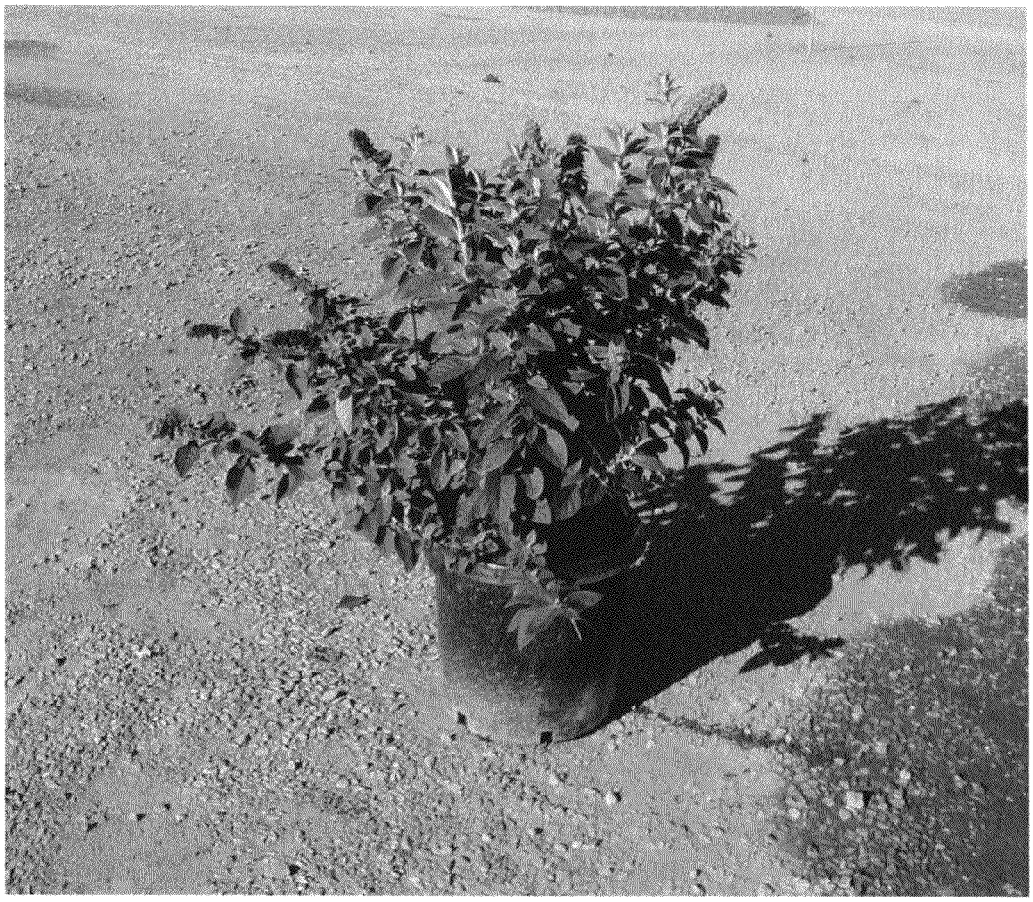
FIG. 1 shows a whole plant, including the habit, foliage and inflorescence.
Figure 2:
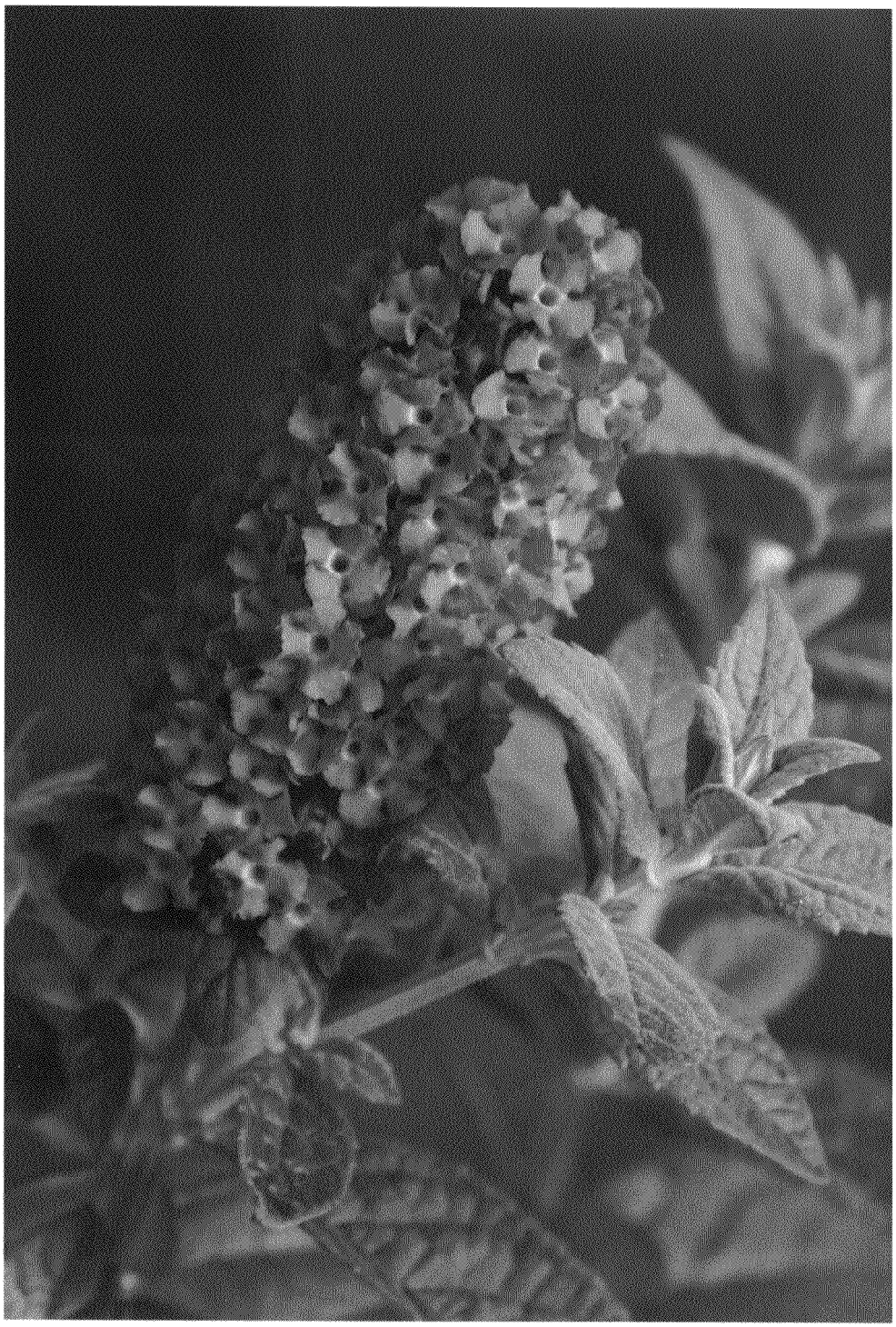
FIG. 2 shows a close-up of the inflorescence and buds.

The following detailed descriptions set forth the distinctive characteristics of 'Hinebud2'. The data which defines these characteristics were collected from asexual reproductions carried out in Winters, Calif. The plant history was taken in January 2012 on one and one-half year old plants grown in a greenhouse and outdoors in Winters, Calif. Color references were taken under natural light and are to The R.H.S. Colour Chart of The Royal Horticultural Society of London (R.H.S.), fifth edition (2007). Texture descriptions were taken using a dissecting microscope.

DESCRIPTION OF THE NEW PLANT

Classification:

*Family.*—Scrophulariaceae.

*Botanical name.*—*Buddleia* hybrid (complex hybrid of *Buddleia davidii*×*Buddleia alternifolia*×*Buddleia caryopterifolia*×*Buddleia lindleyana*×*Buddleia crispa*).

*Common name.*—Butterfly bush.

*Denomination.*—'Hinebud2'.

Plant:

*Form.*—Bush.

*Habit.*—Upright and dense.

*Height* (*measured from the top of the soil, with the plant cut back after* 1 *year*).—183.0 cm.

*Width* (*horizontal plant diameter*).—153.0 cm.

*Time to produce a finished plant.*—3 months from a softwood cutting.

*Outdoor plant performance.*—Excellent and prefers full sun.

*Time to initiate and develop roots.*—About 12 days using rooting hormones between 3,000 to 6,000 ppm.

*Root description and habit.*—White, fibrous, dense and branching.

*Propagation type.*—Softwood cuttings.

Lateral branches:

*Quantity per plant.*—Approximately 30 to 40.

*Length.*—About 60.0 cm to 90.0 cm.

*Internode length.*—6.0 cm to 7.0 cm.

*Diameter (from midpoint).*—0.8 cm.

*Color.*—RHS 144A for mature stems.

*Strength.*—Strong and flexible.

*Texture.*—Slightly pubescent.

*Anthocyanin.*—RHS 176B.

Leaves:

*Quantity of leaves per branch.*—12 to 14.

*Arrangement.*—Opposite, alternating 90° after each node.

*Length.*—6.0 cm to 12.0 cm.

*Width.*—4.0 cm to 6.0 cm.

*Shape.*—Broadly lanceolate.

*Apex.*—Broadly acute.

*Base.*—Attenuate.

*Margin.*—Crenate.

*Color, immature.*—Upper surface: RHS 138B. Lower surface: RHS 148D.

*Color, mature.*—Upper surface: RHS 139A. Lower surface: RHS 148B.

*Texture.*—Upper surface: Colliculate with stellate hairs and glandular bodies. Lower surface: Extremely dense matted stellate hairs with glandular bodies.

*Venation type.*—Reticulate.

*Venation color.*—Upper surface: RHS N144D. Lower surface: RHS 139D.

*Petiole.*—Color: RHS 147C. Length: 0.1 cm. Diameter: 0.25 cm. Strength: Flexible. Texture: Pubescent.

Inflorescence:

*Height.*—7.0 cm to 12.0 cm.

*Width.*—4.0 cm to 6.0 cm.

*Bud.*—Color: RHS 86A. Shape: Conical. Height: 1.0 cm. Diameter: 0.4 cm.

*Flower.*—Type and habit: Single and salverform shaped flowers arranged in compound terminal panicles; flowers face upright and outward; panicles are roughly conical with a slight outward curvature and a rounded apex. Fragrance: Sweetly scented. Flowering season: May to September. Lastingness of inflorescence on the plant: About 7 to 12 days. Depth: 1.0 cm. Diameter: 1.2 cm. Quantity per inflorescence: 300 to 600. Petals: Arrangement and quantity per flower: Four arranged in a single whorl but occasionally, there are 5 petals on flowers on the distal portion of the inflorescence; the petals fused into a narrow tube. Length: 0.5 cm. Width: 0.6 cm. Shape: Reniform. Apex: Truncate and obtuse, sometimes emarginate. Base: Fused. Margin: Crenate. Texture: Upper surface: Colliculate. Lower surface: Colliculate with sparse stellate trichomes. Color, when opening: Upper surface: RHS 86B. Lower surface: RHS N82B. Color, when open: Upper surface: RHS N87A. Lower surface: RHS N87B. Tube: Length: 0.9 cm. Width: 0.2 cm. Color: Inside: RHS N34A. Outside: RHS N92A. Texture: Inside: Colliculate with long, upward-setose pointed hairs. Outside: Colliculate with stellate hairs. Calyx: Arrangement and quantity: Four sepals (occasionally 5 on flowers on the distal end of the inflorescence) arranged in a single whorl and fused halfway up from the base. Shape: Tubular, fitting snugly over the corolla tube. Sepals: Length: 0.4 cm. Width: 0.1 cm. Shape: Lanceolate but fused halfway up from the base. Apex: Broadly acute. Base: Fused with other sepals. Margin: Slightly sinuate. Texture: Upper surface: Lepidote with stellate hairs. Lower surface: Colliculate with more sparse stellate hairs than the upper surface. Color: Upper surface: RHS 147C. Lower surface: RHS 146B. Peduncle: Length: 5.0 cm to 7.5 cm. Diameter: 0.2 cm. Strength: Flexible. Color: RHS 142D. Texture: Pubescent. Pedicel: Length: 0.2 cm to 0.4 cm. Diameter: 0.15 cm. Color: RHS 139D. Texture: Pubescent.

Reproductive organs:

*Stamens.*—Quantity per flower: Mostly 4, occasionally 5. Filament: Completely fused to inside of corolla tube; cannot determine length or color. Anther: Length: 0.12 cm. Color: RHS 197D. Pollen amount: Sparse. Pollen color: RHS 197D.

*Pistil.*—Quantity per flower: 1. Length: 0.15 cm. Stigma: Shape: Club-shaped, slight bilateral cleavage at the distal end. Color: RHS 137A. Style: Length: 0.1 cm. Color: RHS 192A. Ovary: Color: RHS 192A.

Fruit and seed set: Sparse seed set. Seeds are RHS 158C, the shape is long and narrow, about 0.025 cm by 0.01 cm.

Disease and insect resistance: Susceptible to spider mites.

COMPARISON WITH PARENTAL AND COMMERCIAL VARIETY

'Hinebud2' differs from the un-named female *Buddleia* parent (unpatented) in that 'Hinebud2' has larger leaves and an upright habit, while the female parent has smaller leaves and a prostrate habit.

'Hinebud2' differs from the male *Buddleia* parent 'Podaras #12' (U.S. Plant Pat. No. 22,098) in that 'Hinebud2' is a taller and has a greater horizontal plant diameter (height is 183.0 cm and width or horizontal plant diameter is 153.0 cm) than 'Podaras #12' (height is approximately 23.0 cm and width is 38.0 cm to 56.0 cm).

'Hinebud2' differs from the commercial comparison 'Blue Chip' (U.S. Plant Pat. No. 19,991) in that 'Hinebud2' has longer internodes (6.0 cm to 7.0 cm) and longer peduncles (5.0 cm to 7.5 cm) than 'Blue Chip' (internode is 3.6 cm in length and peduncles are 2.4 cm in length).

I claim:

1. A new and distinct variety of *Buddleia* plant as shown and described herein.

* * * * *